United States Patent
Di Maiuta et al.

(10) Patent No.: US 10,221,316 B2
(45) Date of Patent: Mar. 5, 2019

(54) PROCESS TO PRESERVE AQUEOUS PREPARATIONS OF MINERAL MATERIALS, PRESERVED AQUEOUS PREPARATIONS OF MINERAL MATERIALS AND USE OF PRESERVATIVE COMPOUNDS IN AQUEOUS PREPARATIONS OF MINERAL MATERIALS

(75) Inventors: Nicola Di Maiuta, Zuchwil (CH); Patrick Schwarzentruber, Habsburg (CH)

(73) Assignee: Omya International AG, Oftringen (CH)

(*) Notice: Subject to any disclaimer, the term of this patent is extended or adjusted under 35 U.S.C. 154(b) by 85 days.

(21) Appl. No.: 13/637,991

(22) PCT Filed: Mar. 31, 2011

(86) PCT No.: PCT/EP2011/055023
§ 371 (c)(1),
(2), (4) Date: Nov. 6, 2012

(87) PCT Pub. No.: WO2011/124521
PCT Pub. Date: Oct. 13, 2011

(65) Prior Publication Data
US 2013/0137778 A1 May 30, 2013

Related U.S. Application Data

(60) Provisional application No. 61/342,617, filed on Apr. 16, 2010.

(30) Foreign Application Priority Data

Apr. 9, 2010 (EP) ..................................... 10159511

(51) Int. Cl.
| C09C 1/02 | (2006.01) |
|---|---|
| A01N 37/04 | (2006.01) |
| A01N 55/02 | (2006.01) |
| A01N 59/00 | (2006.01) |
| A01N 59/06 | (2006.01) |
| A01N 59/08 | (2006.01) |
| A61K 8/04 | (2006.01) |
| A61K 8/19 | (2006.01) |
| C02F 1/50 | (2006.01) |
| D21H 17/66 | (2006.01) |
| D21H 21/36 | (2006.01) |
| C02F 103/28 | (2006.01) |

(52) U.S. Cl.
CPC .............. *C09C 1/022* (2013.01); *A01N 37/04* (2013.01); *A01N 55/02* (2013.01); *A01N 59/00* (2013.01); *A01N 59/06* (2013.01); *A01N 59/08* (2013.01); *A61K 8/044* (2013.01); *A61K 8/19* (2013.01); *C02F 1/50* (2013.01); *D21H 17/66* (2013.01); *D21H 21/36* (2013.01); *A61K 2800/524* (2013.01); *C01P 2004/61* (2013.01); *C01P 2004/62* (2013.01); *C01P 2006/22* (2013.01); *C02F 2103/28* (2013.01); *Y02A 50/359* (2018.01)

(58) Field of Classification Search
CPC ..................................... A61K 8/19; C09C 1/02
See application file for complete search history.

(56) References Cited

U.S. PATENT DOCUMENTS

| 3,983,252 A | 9/1976 | Buchalter | |
|---|---|---|---|
| 4,332,692 A * | 6/1982 | Payne et al. | 8/137 |
| 4,655,815 A | 4/1987 | Jakubowski | |
| 4,789,491 A * | 12/1988 | Chang et al. | 510/525 |
| 5,278,248 A | 1/1994 | Egraz et al. | |
| 5,496,398 A | 3/1996 | Drew et al. | |
| 6,074,473 A * | 6/2000 | Nichols et al. | 106/469 |
| 6,395,703 B2 * | 5/2002 | Scepanski | 510/445 |
| 6,613,142 B1 * | 9/2003 | D'Almeida | C04B 28/08 106/789 |
| 2001/0009682 A1 | 7/2001 | Whiteley et al. | |
| 2006/0111410 A1 | 5/2006 | Wachtler et al. | |
| 2007/0053946 A1 | 3/2007 | Peyton et al. | |
| 2008/0146715 A1 * | 6/2008 | Yuan | C09C 1/021 524/425 |

FOREIGN PATENT DOCUMENTS

| CN | 101648824 A | 12/2010 | |
|---|---|---|---|
| DE | 10109979 A1 | 9/2002 | |
| EP | 0161869 A2 | 11/1985 | |
| EP | 1547621 A2 | 6/2005 | |
| EP | 1623725 A2 | 2/2006 | |
| EP | 1661587 A1 | 5/2006 | |
| EP | 2108260 A2 | 10/2009 | |
| GB | 646030 A * | 11/1950 | ............... D21H 5/16 |
| GB | 1443786 A | 7/1976 | |
| JP | 59144703 A | 8/1984 | |
| WO | 0039222 A1 | 7/2000 | |
| WO | 0185659 A1 | 11/2001 | |
| WO | 02052941 A1 | 7/2002 | |
| WO | 04040979 A1 | 5/2004 | |
| WO | 04083316 A1 | 9/2004 | |
| WO | 05121257 A2 | 12/2005 | |
| WO | 06079911 A1 | 8/2006 | |
| WO | 09074492 A1 | 6/2009 | |

OTHER PUBLICATIONS

International Search Report dated Jul. 12, 2011 for PCT Application No. PCT/EP2011/055023.
Written Opinion of the International Searching Authority dated Jul. 12, 2011 for PCT Application No. PCT/EP2011/055023.
Thomson WPI 1984: XP-002588337.
Thomson WPI 2010: XP002588338.

* cited by examiner

*Primary Examiner* — Kyle A Purdy
(74) *Attorney, Agent, or Firm* — Amster, Rothstein & Ebenstein LLP

(57) ABSTRACT

The present invention refers to a process for preserving an aqueous preparation of mineral material like e.g. calcium carbonate preparations, and to the use of a composition as a preservative in an aqueous preparation of mineral materials.

25 Claims, No Drawings

PROCESS TO PRESERVE AQUEOUS PREPARATIONS OF MINERAL MATERIALS, PRESERVED AQUEOUS PREPARATIONS OF MINERAL MATERIALS AND USE OF PRESERVATIVE COMPOUNDS IN AQUEOUS PREPARATIONS OF MINERAL MATERIALS

CROSS-REFERENCE TO RELATED APPLICATIONS

This application is a U.S. national phase of PCT Application No. PCT/EP2011/055023, filed Mar. 31, 2011, which claims priority to European Application No. 10159511.4, filed Apr. 9, 2010 and U.S. Provisional Application No. 61/342,617, filed Apr. 16, 2010.

The present invention relates to a process for preserving an aqueous preparation of mineral materials, to preserved aqueous preparations obtained by this process and to the use of preservative compounds in aqueous preparations of mineral materials.

In practice, aqueous preparations of mineral materials are used extensively in processes to prepare paper, paint, rubber and plastics, among other applications. For example, suspensions or dispersions of calcium carbonate, talc or kaolin are used in the paper industry in large amounts as filler and/or as a component of paper coating formulations. Typical aqueous preparations of mineral materials are characterized in that they comprise water, one or more mineral materials and optionally further additives, such as dispersing and/or grinding aid agents, forming a suspension or dispersion with a solids content of 1 to 80% by dry weight relative to the total weight of the preparation. Polymers and copolymers which may be used as dispersant and/or grinding aid agents in such preparation are, for example, described in U.S. Pat. No. 5,278,248.

The aforementioned aqueous preparations are often subject to contamination by microorganisms such as aerobic and anaerobic bacteria resulting in changes in the preparation properties, such as changes in viscosity and/or pH, discolorations or reductions in other quality parameters, which negatively affect their commercial value. Therefore, the manufacturers of such aqueous preparations usually take measures for disinfecting and preserving the suspensions or dispersions. For example, EP 1 139 741 describes aqueous suspensions or dispersions of minerals, fillers and/or pigments, containing a microbiocidal agent in the form of a solution and derivatives of phenol in partially neutralized form. WO 01/85659 mentions aqueous formulations containing one or more phenolates and at least one crystallization inhibitor that may be used to preserve mineral slurries. U.S. Pat. No. 5,496,398 relates to a process for the reduction of microorganisms in kaolin clay slurries by a combination of low temperature heat and reduced levels of a microbiocidal agent. WO 02/052941 describes biocide compositions for incorporation into paints, coating, plasters and plastics comprising at least one metal oxide and at least one metal salt. U.S. Pat. No. 4,655,815 mentions a antimicrobial composition comprising a formaldehyde donor.

WO 2004/040979 A1 relates to synergic antimicrobial mixtures containing 1,2-benzisothiazolinone (BIT) and benzylhemiformal (BHF). The corresponding mixtures are used, for example, for slurries of pigments.

For the purpose of the present invention, chemical means for disinfection are referred to as "disinfectants" and are understood to comprise substances that destroy microorganisms. For example, US 2001/0009682 relates to disinfectant concentrates having improved biocidal activity which may contain an aldehyde such as glutaraldehyde, a glycol and a lithium based buffer. WO 2006/079911 mentions a process for disinfection and/or preservation and/or reduction and/or control of microbial contamination of aqueous dispersions and/or suspensions of mineral matter, having at least one stage of increasing the $OH^-$ ion concentration of the aqueous dispersions or suspensions to a value greater than or equal to $1 \times 10^{-2}$ mole/l, and at least one stage of dispersing and/or grinding the aqueous dispersions and/or suspensions.

For the purpose of the present invention, chemical means for preservation are referred to as "preservatives" and are understood to comprise substances inhibiting the growth and reproduction of microorganisms. For example, US 2006/0111410 mentions a mixture comprising 1,2-benzisothiazolinone (BIT) and tetramethylolacetylenediurea (TMAD) for protecting industrial materials and products against attack by microorganisms.

With regards to this latter class of preservatives used in aqueous preparations of mineral materials, the classical example widely used in industry is orthophenylphenol (OPP).

However, a recent European Council Directive has made it known that OPP will be newly classified as a pesticide in food, feed and plant protection applications. This new classification implies that many users of aqueous mineral preparations requiring preservation will prefer aqueous mineral preparations preserved with OPP alternatives that are not associated with toxic residues on application, such as applications involving food contact, nor with toxic residues in waste products such as waste water. Any manufacturing plant producing aqueous preparations of mineral materials having one or more customers implementing such preparations in food, feed and plant protection application will then be obliged to globally implement an OPP alternative for essentially all customers due to the risk of OPP contamination throughout the plant.

Thus, there is a pressing need for adequate compositions providing sufficient preservation of aqueous preparations of mineral materials without implementing substances causing toxic residues.

In answer, the application has surprisingly found a preservation system meeting these needs of the skilled man. Accordingly, first object of the present invention resides in a process for preserving an aqueous preparation of mineral material, characterised in that the process comprises the following steps:

(a) providing an aqueous preparation of at least one mineral material;

(b) adding to the aqueous preparation of step a) one or more sources of lithium ions in an amount such that the total amount of lithium ions in the aqueous preparation is from 750 to less than 3 000 ppm, calculated relative to the water in the preparation;

(c) adding to the aqueous preparation of step a) one or more sources of sodium and/or potassium and/or magnesium ions in an amount such that the total amount of sodium and/or potassium and/or magnesium ions in the aqueous preparation is from 3 000 to less than 7 500 ppm, calculated relative to the water in the preparation, where steps (b) and (c) may be carried out simultaneously, or separately in any order.

According to the present invention, lithium, sodium, potassium and magnesium ion contents in water can be evaluated by filtering off the solids in the suspension by membrane filtration (pore size of 0.2 microns) and measuring the content of these ions in the filtrate by liquid chromatography.

According to the present invention, preservation is evaluated as a lack of "significant growth" of bacteria over time starting from an aqueous preparation of mineral material having a cfu/ml value (colony forming unit per milliliter) of less than $10^4$ cfu/ml. Said lithium and sodium ions are added to this starting aqueous preparation of mineral material. Thereafter, the aqueous preparation is inoculated with bacteria and the cfu/ml development is determined as described in the examples section hereafter. Significant growth means a growth of bacteria of greater than the error associated with the cfu/ml measurement technique.

The use of sodium bicarbonate alone as an inhibitor of bacterial growth in food has been described in Corral, L. et al. ("Research Note: Antimicrobial Activity", *Journal of Food Science*, Volume 53, No. 3, 1988, page 981). Table 1 of this publication shows that sodium bicarbonate amounts required to inhibit growth are of the order of 1%. No mention is made of any use of lithium ions to allow far lower amounts of sodium bicarbonate to be employed in the context of an aqueous preparation of mineral materials. Moreover, the bacterial species targeted are different from those typically found in the aqueous preparations of the present invention.

Similarly, Wijnker J. et al. ("Antimicrobial properties of salt (NaCl) used for the preservation of natural casings", *Food Microbiology*, Volume 23, 2006, pages 657-662) disclose the use of sodium chloride as a preservative in food applications. Again, no mention is made of any use of lithium ions and the targeted bacterial differ from those typical of an aqueous preparation of mineral material.

Finally, also in the context of food applications, sodium hydrogen carbonate is referred to in combination with ovotransferrin for providing antimicrobial activity against *L. monocytogenes* and *E. coli*.

Relative to lithium ions, these are disclosed as enhancers of aldehyde-releasing and/or aldehyde-based biocides in EP 2 108 260.

EP 1 623 725 discloses a kit to prepare a germicidal solution comprising phthalaldehyde and an enhancer for the phthalaldehyde, where said enhancer may be a halide salt. EP 1 547 621 similarly mentions a germicidal dialdehyde enhanced by a halide salt.

EP 1 661 587 refers to a method of sealing a germicidal bicarbonate solution in containers.

GB 1 443 786 claims a composition having biocidal and sporicidal activity, which comprises a solvent which is water or a mixtures of water and a lower monohydric alcohol, glutaraldehyde and dissolved quantities of at least one highly ionisable salt of a monovalent or divalent cation base exchangeable with calcium, the composition having a pH of 7 or less.

US 2006/0111410 refers to a mixture of biocidally active compounds, characterized in that it comprises tetramethyloacetylediurea (TMAD) and 1,2-benzothiazoline (BIT) and/or its sodium, potassium or lithium salt.

U.S. Pat. No. 3,983,252 refers to a disinfectant composition comprising a saturated dialdehyde containing from 2 to about 6 carbon atoms; an alkali metal salt of a carboxylic acid containing from 2 to 25 carbon atoms and selected from the group consisting of sodium, potassium or lithium salts of alkanoic acids, sodium, potassium, or lithium salts of alkenoic acids, and sodium, potassium or lithium salts of aromatic acids; and a member selected from the group consisting of lower alkanols containing up to and including 7 carbon atoms, alkanediols containing from 2 to 4 carbon atoms, glycerol and mixtures thereof, said alkali metal salt of a carboxylic acid being present in a weight ratio to said dialdehyde within the range of from about 0.05:1 to about 2:1, said lower alkanol, alkanediol or glycerol being present in a weight ratio to said alkali metal salt of a carboxylic acid within the range of from about 1:0.1 to about 1:3, said composition when dissolved in water providing a solution having a pH of within the range of from about 6 to about 7.4.

Finally, US 2001/0009682 refer to disinfectant concentrates having improved biocidal activity containing an aldehyde, such as glutaraldehyde, a glycol and a lithium based buffer.

Indeed, relative to the latter prior art documents, it is a remarkable advantage of the present invention that no conventional biocide, such as an aldehyde-based biocide, is needed in order to obtain preservation of an aqueous mineral preparation.

Aqueous Mineral Preparation of Step a)

According to step a) of the process of the present invention, an aqueous preparation of at least one mineral material is provided.

Aqueous preparations in the meaning of the present invention comprise filter cakes, suspensions or dispersions having a solids content of 1 to 85%, preferably from 10 to 82%, and more preferably from 20 to 80%, by dry weight relative to the total weight of the aqueous preparation, as measured according to the measurement method provided in the examples section hereafter.

Typically, the aqueous preparations of step a) have a pH value of 6 to 10.5, and preferably of 7 to 10. The aqueous preparations of step a) preferably have a viscosity of from 50 to 800 mPa·s, and more preferably of 80 to 600 mPa·s, as measured according to the measurement methods given in the examples section herebelow.

The mineral material may be natural or synthetic and selected from the group consisting of calcium carbonate, such as ground calcium carbonate and precipitated calcium carbonate, kaolin, kaolinitic clay, calcined kaolinitic clay, talc, calcium sulfate, quartz, attapulgite, montmorillonite, diatomaceous earth, finely divided silica, aluminium oxide, aluminium hydroxide, silicates such as aluminium silicate, pumice, sepiolite, dolomite, composite pigment materials including precipitated calcium carbonate, mica, titanium dioxide, and mixtures thereof.

Preferably, said mineral material is a ground calcium carbonate, such as chalk, limestone, marble or mixtures thereof, a precipitated calcium carbonate, dolomite, kaolin, kaolinitic clay, calcined kaolinitic clay or a mixture thereof.

Calcium carbonate ($CaCO_3$) e.g. is used as a coating and filling pigment, and is notably known to improve some of the optical properties of the final product, such as gloss, opacity or brightness. Calcium carbonate can be of two types: ground or natural calcium carbonate referred to as GCC, and synthetic or precipitated calcium carbonate referred to as PCC. PCC may be rhombohedral and/or scalenohedral and/or aragonitic. The GCC or PCC may additionally be surface treated, for example with fatty acids such as stearic acid and corresponding calcium salts, and/or with siloxane.

"Ground calcium carbonate" (GCC) in the meaning of the present invention is a calcium carbonate obtained from natural sources, such as limestone, marble or chalk or dolomite, and processed through a treatment such as grinding, screening and/or fractionizing by wet and/or dry, for example by a cyclone or classifier.

"Precipitated calcium carbonate" (PCC) in the meaning of the present invention is a synthesized material, generally obtained by precipitation following reaction of carbon dioxide and lime in an aqueous environment or by precipitation of a calcium and carbonate ion source in water.

Said GCC or PCC may, in one embodiment, be surface reacted to form a surface-reacted calcium carbonate, which are materials comprising GCC and/or PCC and an insoluble, at least partially crystalline, non-carbonate calcium salt extending from the surface of at least part of the calcium carbonate. Such surface-reacted products may, for example, be prepared according to WO 00/39222, WO 2004/083316, WO 2005/121257, WO 2009/074492, unpublished European patent application with filing number 09162727.3, and unpublished European patent application with filing number 09162738.0.

Clay refers to crystalline small particles of mainly hydrous silicates of aluminum, sometimes with magnesium and/or iron substitution for all or a part of the aluminium. The main groups of clay minerals are: kaolinite, the main constituent of kaolin; halloysite; illite; montmorillonite and vermiculite. The term "kaolinitic clay" used herein refers to a soft white clay that is composed mainly of the mineral kaolinite.

Kaolin is especially used in the paper industry, which uses them to coat and fill papers and boards and improves some of the optical properties of the final product, such as gloss, opacity or brightness. However, kaolin based products include paints, agricultural compositions, fibre glass products, polymer and rubber compositions, ceramic applications, catalyst supports, pharmaceuticals, cosmetics, adhesives, filter aids, and many more.

The mineral material of said preparation of step a) may have a particle size distribution as conventionally employed for the material(s) involved in the type of product to be produced. For the purpose of the present invention, all particle size measurements are made in accordance with the measurement methods given in the examples section hereafter.

In general, 90% of the particles will have an esd (equivalent spherical diameter) of less than 5 micron. Coarse minerals, filler or pigment materials may have a particle esd generally (i.e., at least 90 wt.-%) in the range of 1 to 5 microns. Fine minerals, filler or pigment materials may have a particle esd generally less than 2 microns, e.g. 50 to 99 wt.-% less than 2 microns and preferably 60 to 90 wt.-% less than 2 microns. It is preferred that the solid particles in the preparation have a $d_{50}$ value of from 0.1 to 5 µm, preferably from 0.2 to 2 µm and most preferably from 0.35 to 1 µm, for example 0.7 µm.

For keeping mineral particles suspended in an aqueous preparation and thus ensuring that the viscosity of the preparation remains substantially the same over time, additives such as dispersing agents may be used. A suitable dispersing agent according to the present invention is preferably made of monomers and/or co-monomers selected from the group consisting of acrylic acid, methacrylic acid, itaconic acid, crotonic acid, fumaric acid, maleic anhydride acid, isocrotonic acid, aconitic acid (cis or trans), mesaconic acid, sinapinic acid, undecylenic acid, angelic acid, canellic acid, hydroxyacrylic acid, acrolein, acrylamide, acrylonitrile, dimethylaminoethyl methacrylate, vinylpyrrolidone, vinylcaprolactam, ethylene, propylene, isobutylene, diisobutylene, vinyl acetate, styrene, α-methyl styrene, methyl vinyl ketone, the esters of acrylic and methacrylic acids and mixtures thereof, wherein poly(acrylic acid) and/or poly (methacrylic acid) are preferred as dispersing agent.

Lithium Ions of Step b)

According to step b) of the process of the present invention, one or more sources of lithium ions are provided to the aqueous preparation of step a) in an amount such that the total amount of lithium ions in the aqueous preparation is from 750 to 3 000 ppm, calculated relative to the water in the preparation.

Said lithium ions should be provided in a form such that on addition to said aqueous preparation of step a), the pH of said aqueous preparation remains in a range such that no dissolution of said mineral material results. For example, in the case of a calcium carbonate suspension having a pH of between 7 and 10, the pH of this suspension should not drop significantly below pH 7 on lithium ion addition, into a pH range implying calcium carbonate dissolution.

Said lithium ions are preferably be provided in a form such that on addition to said aqueous preparation of step a), the viscosity of said aqueous preparation does not exceed 800 mPa·s.

Said lithium ions may be provided in the form of a water soluble lithium compound. Preferably, said water soluble lithium compound is selected from lithium salts, and preferably from lithium carbonate, polymeric salts of lithium and mixtures of lithium carbonate with polymeric salts of lithium. In a most preferred embodiment, said water soluble lithium compound is lithium carbonate.

In the embodiment where said water soluble lithium compound is a mixture of lithium carbonate and polymeric salts of lithium, it is preferred that the weight ratio of said lithium carbonate:polymeric salts of lithium is from 50:50 to 99.9:0.1.

Polymeric salt of lithium are preferably selected from lithium salts of acrylic homopolymers, acrylic copolymers such as copolymers of acrylic acid and maleic acid and/or acrylamide, polyphosphates and mixtures thereof, said polymeric salt of lithium being more preferably a $Li_2Na_2$polyphosphate, lithium-sodium hexamethaphosphate or lithium polyacrylate. $Li_2Na_2$polyphosphate may be prepared by using an ion exchange technique (treatment of a cation exchanger in a column with lithium hydroxide and before passing a water based solution of $Na_4P_2O_7$ from the top to the bottom of the column).

Said polymeric lithium salts are partially or completely neutralized, preferably to a degree of 5 to 100%, preferably to a degree of 25 to 100% and most preferably to a degree of 75 to 100% using a neutralizing agent containing ions of lithium and, optionally other alkali metals and/or alkaline earth metals. It is especially preferred that said polymeric salts of lithium are used wherein preferably at least 40 mole-%, preferably 45 to 80 mole-% and more preferably 95 to 100 mole-%, of the acid sites of said polymeric salts of lithium are neutralized by lithium.

In an especially preferred embodiment the acidic sites of the polymeric lithium salt are neutralized using a neutralizing agent containing only lithium or lithium ions in combination with magnesium ions.

Neutralized polyacrylates and/or polymethacrylates with an average molecular weight of not more than 50,000, preferably with an average molecular weight in the range from 1,000 to 25,000 and more preferably in the range from 3,000 to 12,000 are especially suitable.

It is to be noted that the aforementioned figures reflect the amount of lithium ions being added to the aqueous preparation, and do not cover any lithium ions which may naturally be present in the aqueous preparation. However, the amount of naturally occurring lithium ions in e.g. a calcium carbonate slurry usually is negligible and well below 50 ppm, based on the mineral material content of the aqueous preparation.

In a preferred embodiment, said lithium ions are provided to the aqueous preparation of step a) in an amount such that the total amount of lithium ions in the aqueous preparation is from 750 to 1 500 ppm, calculated relative to the water in the preparation.

The optimum amount to be employed within the defined ranges can be determined by preliminary tests and test series on a laboratory scale and by supplementary operational tests.

Sodium Ions of Step c)

According to step c) of the process of the present invention, one or more sources of sodium and/or potassium and/or magnesium ions are added to said aqueous preparation of step a) in an amount such that the total amount of sodium and/or potassium and/or magnesium ions in the aqueous preparation is from 3 000 to 7 500 ppm, calculated relative to the water in the preparation.

Said sodium and/or potassium and/or magnesium ions should be provided in a form such that on addition to said aqueous preparation of step a), the pH of said aqueous preparation remains in a range such that no dissolution of said mineral material results. For example, in the case of a calcium carbonate suspension having a pH of between 7 and 10, the pH of this suspension should not drop significantly below pH 7 on addition of said sodium and/or potassium and/or magnesium ions, into a pH range implying calcium carbonate dissolution.

Said sodium and/or potassium and/or magnesium ions are preferably be provided in a form such that on addition to said aqueous preparation of step a), the viscosity of said aqueous preparation does not exceed 800 mPa·s.

Said sodium and/or potassium and/or magnesium ions may be provided in the form of a water soluble sodium and/or potassium and/or magnesium compound. Preferably, said water soluble sodium and/or potassium and/or magnesium compound is selected from sodium and/or potassium and/or magnesium carbonate, sodium and/or potassium and/or magnesium chloride, mixtures of sodium and/or potassium and/or magnesium chloride with polymeric salts of sodium and/or potassium and/or magnesium, and mixtures of sodium and/or potassium and/or magnesium carbonate with polymeric salts of sodium and/or potassium and/or magnesium. In a most preferred embodiment, said water soluble sodium and/or potassium and/or magnesium compound is sodium and/or potassium and/or magnesium carbonate. In a most preferred embodiment, said sodium and/or potassium and/or magnesium compound is sodium carbonate.

In the embodiment where said water soluble sodium and/or potassium and/or magnesium compound is a mixture of sodium and/or potassium and/or magnesium carbonate and polymeric salts of sodium and/or potassium and/or magnesium, it is preferred that the weight ratio of said sodium and/or potassium and/or magnesium carbonate:polymeric salts of sodium and/or potassium and/or magnesium is from 80:20 to 99.9:0.1.

Polymeric salt of sodium and/or potassium and/or magnesium are preferably selected from sodium and/or potassium and/or magnesium salts of acrylic homopolymers, acrylic copolymers such as copolymers of acrylic acid and maleic acid and/or acrylamide, polyphosphates and mixtures thereof, said polymeric salt of sodium being more preferably a $Li_2Na_2$polyphosphate, lithium-sodium hexamethaphosphate or lithium polyacrylate. $Li_2Na_2$polyphosphate may be prepared by using an ion exchange technique (treatment of a cation exchanger in a column with lithium hydroxide and before passing a water based solution of $Na_4P_2O_7$ from the top to the bottom of the column).

Said polymeric sodium and/or potassium and/or magnesium salts are partially or completely neutralized, preferably to a degree of 5 to 100%, preferably to a degree of 25 to 100% and most preferably to a degree of 75 to 100% using a neutralizing agent containing ions of sodium and/or potassium and/or magnesium and, optionally other alkali metals and/or alkaline earth metals. It is especially preferred that said polymeric salts of sodium and/or potassium and/or magnesium are used wherein preferably at least 40 mole-%, preferably 45 to 80 mole-% and more preferably 95 to 100 mole-%, of the acid sites of said polymeric salts of sodium and/or potassium and/or magnesium are neutralized by sodium and/or potassium and/or magnesium.

In an especially preferred embodiment the acidic sites of the polymeric sodium and/or potassium and/or magnesium salts are neutralized using a neutralizing agent containing only sodium or sodium ions in combination with magnesium ions.

Neutralized polyacrylates and/or polymethacrylates with an average molecular weight of not more than 50,000, preferably with an average molecular weight in the range from 1,000 to 25,000 and more preferably in the range from 3,000 to 12,000 are especially suitable.

It is to be noted that the aforementioned figures reflect the amount of sodium and/or potassium and/or magnesium ions being added to the aqueous preparation, and do not cover any sodium and/or potassium and/or magnesium ions which may naturally be present in the aqueous preparation. However, the amount of naturally occurring sodium and/or potassium and/or magnesium ions in e.g. a calcium carbonate slurry usually is negligible and below 50 ppm, based on the mineral material content of the aqueous preparation.

In a preferred embodiment, said sodium and/or potassium and/or magnesium ions are provided to the aqueous preparation of step a) in an amount such that the total amount of sodium ions in the aqueous preparation is from 5 000 to 7 000 ppm, calculated relative to the water in the preparation.

The optimum amount to be employed within the defined ranges can be determined by preliminary tests and test series on a laboratory scale and by supplementary operational tests.

Order of Steps

Said lithium ions of step b) and said sodium and/or potassium and/or magnesium ions of step c) may be added to the aqueous preparation of step a) in any order. For example, they may be added together or separately before and/or during storage or before and/or during transport of the aqueous preparations, in a manner known by the skilled person.

In one embodiment, said lithium ions of step b) and said sodium and/or potassium and/or magnesium ions of step c) are added simultaneously. In this embodiment, said lithium ions of step b) and said sodium and/or potassium and/or magnesium ions of step c) may be pre-mixed prior to addition to said aqueous preparation of step a).

In an alternative embodiment, said lithium ions of step b) and said sodium and/or potassium and/or magnesium ions of step c) are added separately. In the case where said lithium ions are provided via a polymeric salt, it is preferred that the polymeric salt of lithium be added prior to said sodium and/or potassium and/or magnesium ions. In the case where said sodium and/or potassium and/or magnesium ions are provided in part via a polymeric salt, it is preferred that the polymeric salt of sodium and/or potassium and/or magnesium be added prior to said lithium ions.

It is preferred that said lithium ions and said sodium and/or potassium and/or magnesium ions are added to said aqueous preparation of step a) under mixing.

Additional Process Steps

In addition to said lithium ions and said sodium and/or potassium and/or magnesium ions, conventional biocides may additionally be added to said aqueous preparation of mineral material. However, in a more preferred embodiment, no biocide in addition to the biocide formed on combining lithium with magnesium and/or sodium and/or potassium is employed in the process of the present invention.

In the less preferred embodiment where a conventional biocide is employed, it is preferred that said biocide is a disinfectant, in which case it is most preferred that said disinfectant is added prior to said lithium and sodium and/or magnesium and/or potassium ions. Said disinfectant may additionally be dosed following addition of said lithium and sodium and/or magnesium and/or potassium ions.

Said biocide is preferably selected from aldehyde-based biocides, aldehyde-releasing biocides, isothiazoline biocide and mixtures thereof.

In accordance with the present invention, an "aldehyde-based biocide" refers to a biocide which has one or more aldehyde-group. The aldehyde-based biocide of the present invention is preferably selected from the group consisting of formaldehyde, acetaldehyde, glyoxal, succinaldehyde, glutaraldehyde, 2-propenal, phthalic dialdehyde and mixtures thereof, and preferably is formaldehyde, glutaraldehyde and mixtures thereof.

In accordance with the present invention, an "aldehyde-releasing biocide" refers to a compound which is able to release mono- di-, and/or tri-aldehyde. Preferred aldehyde-releasing biocides according to the present invention include formaldehyde-releasing biocides, acetaldehyde-releasing biocides, succinaldehyde-releasing biocides, 2-propenal-releasing biocides and mixtures thereof.

According to another embodiment, the aldehyde-releasing compound is selected from the group consisting of benzyl alcoholmono(poly)-hemiformal, ethyleneglycol-hemiformal (EGHF), [1,2-Ethanediylbis(oxy)]-bis-methanol, tetrahydro-1,3,4,6-tetrakis(hydroxylmethyl)imidazo[4,5-d]imidazole-2,5 (1H,3H)-dione (also commonly referred to as TetraMethylolAcetyleneDiurea TMAD) and mixtures thereof.

In accordance with the present invention, an "isothiazoline biocide" refers to a biocide which comprises at least one isothiazoline group. A preferred isothiazoline biocide is 2-methyl-4-isothiazoline-3-one (MIT), 5-chloro-2-methyl-2H-isothiazolin-3-one (CIT), 1,2-benzisothiazoline-3-one (BIT), or mixtures thereof.

According to another preferred embodiment of the present invention, the aldehyde-releasing and/or aldehyde-based biocide is used together with biocides selected from the group consisting of 5-chloro-2-methyl-2H-isothiazolin-3-one (CIT), 2-methyl-2H-isothiazolin-3-one (MIT) and mixtures thereof.

In the case where biocide selected from aldehyde-based biocides, aldehyde-releasing biocides, isothiazoline biocide and mixtures thereof is employed, said biocide may advantageously be combined with a monoalcohol primary alkanol amine as described in unpublished European patent application filed under number 09178228.4.

Moreover, said process may comprise a step, subsequent to addition of said sodium and/or potassium and/or magnesium ions and said lithium ions, of drying said aqueous preparation to obtain a dry product.

Obtained Preserved Preparation

Another object of the present invention resides in a preserved aqueous preparation obtained by the process of the present invention.

According to the present invention, it is especially preferred that the aqueous preparation obtained by the process of the present invention is preserved relative to bacteria selected from the group consisting of *Thermus* sp., *Propionibacterium* sp., *Rhodococcus* sp., *Panninobacter* sp., *Caulobacter* sp., *Brevundimonas* sp., *Asticcacaulis* sp., *Sphingomonas* sp., *Rhizobium* sp., *Ensifer* sp., *Bradyrhizobium* sp., *Tepidimonas* sp., *Tepidicella* sp., *Aquabacterium* sp., *Pelomonas* sp., *Alcaligenis* sp., *Achromobacter* sp., *Ralstonia* sp., *Limnobacter* sp., *Massilia* sp., *Hydrogenophaga* sp., *Acidovorax* sp., *Curvibacter* sp., *Delftia* sp., *Rhodoferax* sp., *Alishewanella* sp., *Stenotrophomonas* sp., *Dokdonella* sp., *Methylosinus* sp., *Hyphomicrobium* sp., *Methylosulfomonas* sp., *Methylobacteria* sp., *Pseudomonas* sp. and mixtures thereof, and more preferably contains bacteria selected from the group consisting of *Pseudomonas putida*, *Pseudomonas mendocina*, *Pseudomonas fluorescens*, *Pseudomonas alcaligenes*, *Pseudomonas pseudoalcaligenes*, *Pseudomonas entomophila*, *Pseudomonas syringae*, *Methylobacterium extorquens*, *Methylobacterium radiotolerants*, *Methylobacterium dichloromethanicum*, *Methylobacterium organophilu*, *Hyphomicrobium zavarzini* and mixtures thereof.

Preferably, the preservation means that the treated aqueous preparation maintains a cfu/ml value of less than $10^4$ cfu/ml, more preferably of less than $10^3$ cfu/ml, and even more preferably of less than $10^2$ cfu/ml on contamination with any of said bacteria.

Preferably, the inventive process and use provide preservation of aqueous preparations for a time period of at least 2 days, more preferably for at least 4 days, still more preferably for at least 6 days and most preferably for at least 8 days.

Said preserved aqueous preparation obtained by the process of the present invention may find applications in paper making, such as in based paper making and/or in paper coating formulations, and in paint formulations.

Said preserved aqueous preparation obtained by the process of the present invention may be dried to obtain a dry product. Such dry products notably find applications in plastic, food, feed and cosmetic applications.

Use of a Preservative

The present invention also refers to the use of a composition comprising
(a) one or more sources of lithium ions in an amount such that the total amount of lithium ions in the aqueous preparation is from 750 to less than 3 000 ppm, calculated relative to the water in the preparation, and
(b) adding to the aqueous preparation of step a) one or more sources of sodium and/or potassium and/or magnesium ions in an amount such that the total amount of sodium ions in the aqueous preparation is from 3 000 to less than 7 500 ppm, calculated relative to the water in the preparation;
as a preservative in an aqueous preparation of mineral materials.

In a preferred embodiment, no further additive providing biocidal activity is employed.

The following examples may additionally illustrate the invention, but are not meant to restrict the invention to the exemplified embodiments. The examples below show the good microbiological preservation of the aqueous preparations of minerals materials according to the invention.

EXAMPLES

In all of the following examples, the particle size distribution characteristics are measured using a Sedigraph™

5100 of Micromeritics Instrument Corporation. The method and the instrument are known to the skilled person and are commonly used to determine grain size of fillers and pigments. The measurement is carried out in an aqueous solution of 0.1 wt % $Na_4P_2O_7$. The samples are dispersed using a high speed stirrer and supersonics.

All BET specific surface area measurements, quoted in $m^2/g$, are measured according to ISO 4652.

All Brookfield-viscosities are measured with a Brookfield DV-II Viscometer equipped with a LV-3 spindle at a speed of 100 rpm and room temperature (20±3° C.).

All biocide and lithium, sodium, magnesium and potassium amounts quoted in ppm represent mg values per kilogram of water in the aqueous preparation.

All quoted bacterial counts (values are in cfu/ml) in the Tables herebelow are determined after 5 days following plate-out and in accordance with counting method described in "Bestimmung von aeroben mesophilen Keimen", Schweizerisches Lebensmittelbuch, chapter 56, section 7.01, edition of 1985, revised version of 1988.

Example 1: Preparation of Aqueous Mineral Preparations a) Calcium Carbonate Slurry 1

Calcium carbonate slurry 1 was prepared by wet grinding, in a re-circulating, horizontal 1.4 liter attritor ball mill (Dyno-Mill™), a 76.4 wt.-% suspension of north-Norwegian marble having a starting esd (equivalent spherical diameter) of about 45 μm, in the presence of 0.6 wt.-%, based on the total weight of dry calcium carbonate, of a radically polymerized polyacrylic acid (MW 6000 g/Mol, polydispersity 2.6 determined by gel permeation chromatography), wherein 50 mole-% of the carboxylic acid groups are neutralized by sodium and the remaining 50 mole-% of the carboxylic acid groups are neutralized by magnesium. Following grinding, the calcium carbonate in suspension had the following particle size distribution:

| Diameter (μm) | wt.-% |
|---|---|
| <2 | 91.5 |
| <1 | 62.2 |
| <0.2 | 17.9 |

The Brookfield-viscosity of the slurry was determined as 180 mPa·s.

The total soluble magnesium content was 21 ppm and the total soluble sodium content was 927 ppm based on the weight of water in the slurry.

b) Calcium Carbonate Slurry 2

Calcium carbonate slurry 2 was prepared by wet grinding, in a recirculating, horizontal 1.4 liter attritor ball mill (Dyno-Mill™), a 76.1 wt.-% suspension of north-Norwegian marble having a starting esd (equivalent spherical diameter) of about 45 μm, in the presence of 0.6 wt.-%, based on the total weight of dry calcium carbonate, of a radically polymerized polyacrylic acid (MW 6000 g/Mol, polydispersity 2.6 determined by gel permeation chromatography), wherein 100 mole-% of the carboxylic acid groups are neutralized by lithium. Following grinding, the calcium carbonate in suspension had the following particle size distribution:

| Diameter (μm) | wt.-% |
|---|---|
| <2 | 90.5 |
| <1 | 60.2 |
| <0.2 | 15.0 |

The Brookfield-viscosity of the slurry was 130 mPa·s. The total soluble lithium content was 800 ppm based on the weight of water in the slurry.

Example 2: Preservation Activity

The preservation activity of various embodiments of the present invention and of comparison examples was determined in the tests herebelow.

Tests a) Sodium and Lithium Ions 6 000 ppm of sodium ions, based on the weight of the water in the suspension, provided in the form of a 1 M solution of sodium carbonate, were introduced into 50 g samples of calcium carbonate slurry 1. In parallel, control samples of calcium carbonate slurry 1 were prepared without addition of further sodium ions.

The total sodium amounts listed in the Table below were calculated as the amount of sodium ions added as sodium carbonate to calcium carbonate slurry 1, plus the amount of soluble sodium ions added via the polyacrylic acid as mentioned above.

To the indicated samples, lithium ions were provided in the form of lithium carbonate, which was added in the form of a powder and mixed with the suspension in the amounts indicated in the Table below.

Thereafter, half of the samples of calcium carbonate slurry 1 were inoculated with either 1 mL of *Pseudomonas* species or 1 mL of *Pseudomonas* species that are resistant glutaraldehyde-isothiazoline mixtures (said mixtures being in the form of aqueous solutions of 21 weight % glutaraldehyde, 0.25 weight % methylisothiazoline, and 0.75 weight % chloromethylisothiazoline). Each of the samples was incubated at 30° C. for 72 hours. Thereafter, a 1:10 dilution in phosphate buffered saline (PBS) was plated on plate count agar (PCA). These plates were incubated at 30° C. and analysed after 5 days.

| | | *Pseudomonas* sp. | | Resistant *Pseudomonas* species | |
|---|---|---|---|---|---|
| Slurry | Na (ppm on water) | No lithium | 1 350 ppm lithium | No lithium | 750 ppm lithium |
| Calcium carbonate slurry 1 | 927 ppm | >$10^4$ | >$10^4$ | >$10^4$ | >$10^4$ |
| Calcium carbonate slurry 1 | 6 927 ppm | >$10^4$ | <$10^2$ | >$10^4$ | <$10^2$ |

The results of the above table confirm that it is only when sodium is implemented in combination with lithium in the appropriate amount that the bacterial count of the suspension falls to below $10^4$ cfu/ml.

Tests b) Potassium and Lithium Ions 6 000 ppm of potassium ions, based on the weight of the weight of water in the suspension, provided in the form of a 1 M solution of potassium carbonate, was introduced into 50 g samples of calcium carbonate slurry 1. In parallel, control samples of calcium carbonate slurry 1 were prepared in absence of any sodium.

To the indicated samples, lithium ions were provided in the form of lithium carbonate, which was added in the form of a powder and mixed with the suspension in the amounts indicated in the Table below.

Thereafter, half of the samples of calcium carbonate slurry 1 were inoculated with either 1 mL of *Pseudomonas* species or 1 mL of *Pseudomonas* species that are resistant glutaraldehyde-isothiazoline mixtures (said mixtures being in the form of aqueous solutions of 21 weight % glutaraldehyde, 0.25 weight % methylisothiazoline, and 0.75 weight % chloromethylisothiazoline). Each of the samples was incubated at 30° C. for 72 hours. Thereafter, a 1:10 dilution in phosphate buffered saline (PBS) was plated on plate count agar (PCA). These plates were incubated at 30° C. and analysed after 5 days.

| Slurry | K (ppm on water) | *Pseudomonas* sp. No lithium | *Pseudomonas* sp. 1700 ppm lithium | Resistant *Pseudomonas* species No lithium | Resistant *Pseudomonas* species 1050 ppm lithium |
|---|---|---|---|---|---|
| Calcium carbonate slurry 1 | 0 ppm | >$10^4$ | >$10^4$ | >$10^4$ | >$10^4$ |
| Calcium carbonate slurry 1 | 6 000 ppm | >$10^4$ | <$10^2$ | >$10^4$ | <$10^2$ |

The results of the above table confirm that it is only when potassium is implemented in combination with lithium in the appropriate amount that the bacterial count of the suspension falls to below $10^4$ cfu/ml.

Tests c) Sodium and Lithium Ions 2 250 ppm of sodium ions, based on the weight of the weight of water in the suspension, provided in the form of a 1 M solution of sodium carbonate, was introduced into 50 g samples of calcium carbonate slurry 1.

The total sodium amounts listed in the Table below were calculated as the amount of sodium ions added as sodium carbonate to calcium carbonate slurry 1, plus the amount of soluble sodium ions added via the polyacrylic acid as mentioned above.

To the indicated samples, lithium ions were provided in the form of lithium carbonate, which was added in the form of a powder and mixed with the suspension in the amounts indicated in the Table below.

All of samples were then inoculated with 1 mL of *Pseudomonas* species. After inoculation, the samples were incubated at 30° C. for 72 hours. Thereafter, a 1:10 dilution in phosphate buffered saline (PBS) was plated on plate count agar (PCA). These plates were incubated at 30° C. and analysed after 5 days.

| Slurry | Na (ppm on water) | *Pseudomonas* sp. No lithium | *Pseudomonas* sp. 2 250 ppm lithium |
|---|---|---|---|
| Calcium carbonate slurry 1 | 3 177 ppm | >$10^4$ | <$10^2$ |

The results of the above table confirm that it is only when sodium is implemented in combination with lithium in the appropriate amount that the bacterial count of the suspension falls to below $10^4$ cfu/ml.

Tests d) Sodium or Potassium and Lithium Ions—Multiple Inoculations of *Pseudomonas* Species The indicated amount of sodium or potassium ions, based on the weight of the weight of water in the suspension, as listed in the Tables below, provided in the form of a 1 M solutions of sodium or potassium carbonate, was introduced into 50 g samples of calcium carbonate slurry 2. In parallel, control samples of calcium carbonate slurry 1 were prepared in absence of any sodium or potassium.

All of samples were then inoculated three times with 1 mL of *Pseudomonas* species. After each inoculation, the samples were incubated at 30° C. for 72 hours. Thereafter, a 1:10 dilution in phosphate buffered saline (PBS) was plated on plate count agar (PCA). These plates were incubated at 30° C. and analysed after 5 days.

|  | Calcium carbonate slurry 2 | Calcium carbonate slurry 2 | Calcium carbonate slurry 2 | Calcium carbonate slurry 2 |
|---|---|---|---|---|
| Na (ppm on water) | 0 | 3 000 | 4 500 | 6 000 |
| Li (ppm on water) | 800 | 800 | 800 | 800 |
| Inoculation 1 | >$10^4$ | <$10^2$ | <$10^2$ | <$10^2$ |
| Inoculation 2 | >$10^4$ | $10^3$ | <$10^2$ | <$10^2$ |
| Inoculation 3 | >$10^4$ | >$10^4$ | <$10^2$ | <$10^2$ |

|  | Calcium carbonate slurry 2 | Calcium carbonate slurry 2 | Calcium carbonate slurry 2 |
|---|---|---|---|
| K (ppm on water) | 0 | 4 500 | 6 000 |
| Li (ppm on water) | 800 | 800 | 800 |
| Inoculation 1 | >$10^4$ | <$10^2$ | <$10^2$ |
| Inoculation 2 | >$10^4$ | <$10^3$ | <$10^2$ |
| Inoculation 3 | >$10^4$ | >$10^4$ | <$10^2$ |

The results of the above tables confirm that it is only when sodium or potassium is implemented in combination with lithium in the appropriate amount that the bacterial count of the suspension falls to below $10^4$ cfu/ml following at least one innoculation.

Tests e) Sodium or Potassium and Lithium Ions—Multiple Inoculations of biocide-Resistant *Pseudomonas* Species The indicated amount of sodium or potassium ions, based on the weight of the weight of water in the suspension, as listed in the Tables below, provided in the form of a 1 M solutions of sodium or potassium carbonate, was introduced into 50 g samples of calcium carbonate slurry 2. In parallel, control samples of calcium carbonate slurry 1 were prepared in absence of any sodium or potassium.

All of samples were then inoculated three times with 1 mL of *Pseudomonas* species that are resistant glutaraldehyde-isothiazoline mixtures (said mixtures being in the form of aqueous solutions of 21 weight % glutaraldehyde, 0.25 weight % methylisothiazoline, and 0.75 weight % chloromethylisothiazoline). After each inoculation, the samples were incubated at 30° C. for 72 hours. Thereafter, a 1:10 dilution in phosphate buffered saline (PBS) was plated on plate count agar (PCA). These plates were incubated at 30° C. and analysed after 5 days.

| | Calcium carbonate slurry 2 | Calcium carbonate slurry 2 | Calcium carbonate slurry 2 | Calcium carbonate slurry 2 |
|---|---|---|---|---|
| Na (ppm on water) | 0 | 3 000 | 4 500 | 6 000 |
| Li (ppm on water) | 800 | 800 | 800 | 800 |
| Inoculation 1 | >$10^4$ | <$10^3$ | <$10^2$ | <$10^2$ |
| Inoculation 2 | >$10^4$ | >$10^4$ | <$10^3$ | <$10^2$ |
| Inoculation 3 | >$10^4$ | >$10^4$ | >$10^4$ | <$10^2$ |

| | Calcium carbonate slurry 2 | Calcium carbonate slurry 2 | Calcium carbonate slurry 2 | Calcium carbonate slurry 2 |
|---|---|---|---|---|
| K (ppm on water) | 0 | 3 000 | 4 500 | 6 000 |
| Li (ppm on water) | 800 | 800 | 800 | 800 |
| Inoculation 1 | >$10^4$ | <$10^3$ | <$10^3$ | <$10^2$ |
| Inoculation 2 | >$10^4$ | >$10^4$ | >$10^4$ | >$10^4$ |
| Inoculation 3 | >$10^4$ | >$10^4$ | >$10^4$ | >$10^4$ |

The results of the above tables confirm that it is only when sodium or potassium is implemented in combination with lithium in the appropriate amount that the bacterial count of the suspension falls to below $10^4$ cfu/ml following at least one innoculation.

The invention claimed is:

1. A process for preserving an aqueous preparation of mineral material, comprising the following steps:
    (a) providing an aqueous preparation of mineral material at a solids content of 10 to 85% by dry weight relative to the total weight of the aqueous preparation, wherein the mineral material consists of ground calcium carbonate, precipitated calcium carbonate, dolomite, ground calcium carbonate surface treated with a fatty acid, precipitated calcium carbonate surface treated with a fatty acid, surface reacted ground calcium carbonate, surface-reacted precipitated calcium carbonate, or any mixture thereof;
    (b) adding to the aqueous preparation of step (a) one or more sources of lithium ions in an amount such that the total amount of lithium ions in the aqueous preparation is from 750 to less than 3000 ppm, calculated relative to the water in the preparation;
    (c) adding to the aqueous preparation of step a) one or more sources of sodium ions and/or potassium ions in an amount such that the total amount of sodium and/or potassium ions in the aqueous preparation is from 3000 to less than 7500 ppm, calculated relative to the water in the preparation,
    where steps (b) and (c) may be carried out simultaneously, or separately in any order, in order to preserve the aqueous preparation of mineral material so that the aqueous preparation so preserved has a bacterial count of less than $10^4$ cfu/ml.

2. The process according to claim 1, wherein the aqueous preparation has a mineral solids content of 20 to 80%, by dry weight relative to the total weight of the aqueous preparation.

3. The process according to claim 1, wherein the aqueous preparation of step (a) has a pH value of 6 to 10.5.

4. The process according to claim 1, wherein the aqueous preparation of step (a) has a pH value of 7 to 10.

5. The process according to claim 1, wherein the aqueous preparation of step (a) has a viscosity of from 50 to 800 mPa·s.

6. The process according to claim 1, wherein the aqueous preparation of step (a) has a viscosity of from 80 to 600 mPa·s.

7. The process according to claim 1, wherein the mineral material consists of ground calcium carbonate obtained from marble, limestone and/or chalk.

8. The process according to claim 1, wherein the mineral material consists of precipitated calcium carbonate.

9. The process according to claim 1, wherein the source of the lithium ions is a water soluble lithium compound, a lithium salt, lithium carbonate, a polymeric salt of lithium, a mixture of lithium carbonate with a polymeric salt of lithium, or a lithium salt of an acrylic homopolymer, an acrylic copolymer, a copolymer of acrylic acid and maleic acid and/or acrylamide, a polyphosphate, or any mixture thereof.

10. The process according to claim 1, wherein the source of the lithium ions is a polymeric salt of lithium selected from $Li_2Na_2$polyphosphate, lithium-sodium hexametaphosphate, and lithium polyacrylate.

11. The process according to claim 1, wherein the source of the lithium ions is lithium carbonate.

12. The process according to claim 1, wherein the source of the lithium ions is lithium carbonate and a polymeric salt of lithium at a weight ratio of lithium carbonate:polymeric salt of lithium from 50:50 to 99.9:0.1.

13. The process according to claim 1, wherein the lithium ions are provided to the aqueous preparation of step (a) in an amount such that the total amount of lithium ions in the aqueous preparation is from 750 to 1500 ppm, calculated relative to the water in the preparation.

14. The process according to claim 1, wherein the source of the sodium and/or potassium ions is selected from the group consisting of a water soluble sodium compound, a water soluble potassium compound, sodium carbonate, potassium carbonate, sodium chloride, potassium chloride, and any mixture thereof, a mixture of one or more of sodium chloride and potassium chloride with a polymeric salt of one or more of sodium and potassium, and a mixture of one or more of sodium carbonate and potassium carbonate with a polymeric salt of one or more of sodium and potassium.

15. The process according to claim 1, wherein the source of the sodium and/or potassium ions is one or more of sodium carbonate and potassium carbonate.

16. The process according to claim 1, wherein the source of the sodium and/or potassium ions is sodium carbonate.

17. The process according to claim 1, wherein the source of sodium and/or potassium ions is provided to the aqueous preparation of step (a) in an amount such that the total amount of sodium ions in the aqueous preparation is from 5000 to 7000 ppm, calculated relative to the water in the preparation.

18. The process according to claim 1, wherein the source of the lithium ions of step (b) and the source of the sodium and/or potassium ions of step (c) are added simultaneously to the aqueous preparation of step (a).

19. The process according to claim 1, wherein the source of lithium ions of step (b) and source of sodium and/or potassium ions of step (c) are added separately to the aqueous preparation of step (a).

20. The process according to claim 1, wherein when the source of lithium ions is a polymeric salt, the polymeric salt of lithium is added prior to the source of sodium and/or potassium ions.

21. The process according to claim 1, wherein when the source of the sodium and/or potassium ions is a polymeric salt, the polymeric salt of one or more of sodium and/or potassium ions is added prior to the source of lithium ions.

22. The process according to claim 1, wherein no biocide other than the biocide formed by addition of lithium ions and one or more of sodium and/or potassium ions is added.

23. The process according to claim 1, wherein after step (c), the aqueous preparation is dried to obtain a dried product.

24. The process according to claim 1, wherein the mineral material consists of ground calcium carbonate surface treated with a fatty acid or precipitated calcium carbonate surface treated with a fatty acid.

25. The process according to claim 1, wherein the mineral material consists of surface reacted ground calcium carbonate or surface reacted precipitated calcium carbonate.

\* \* \* \* \*